(12) United States Patent
Ito et al.

(10) Patent No.: US 7,174,768 B2
(45) Date of Patent: Feb. 13, 2007

(54) HYDROGEN SENSOR, APPARATUS FOR MEASURING HYDROGEN CONCENTRATION, AND METHOD FOR MEASURING HYDROGEN CONCENTRATION

(75) Inventors: Takuo Ito, Miyagi-Ken (JP); Yasuichi Ono, Miyagi-ken (JP); Toshiaki Konno, Miyagi-ken (JP); Yoshio Nuiya, Saitama-ken (JP)

(73) Assignees: Alps Electric Co., Ltd., Tokyo (JP); Honda Motor Co., Ltd., Tokyo (JP)

( * ) Notice: Subject to any disclaimer, the term of this patent is extended or adjusted under 35 U.S.C. 154(b) by 30 days.

(21) Appl. No.: 11/016,138

(22) Filed: Dec. 17, 2004

(65) Prior Publication Data

US 2006/0131186 A1   Jun. 22, 2006

(30) Foreign Application Priority Data

Dec. 26, 2003 (JP) ............................. 2003-434660

(51) Int. Cl.
   *G01N 25/18*   (2006.01)
(52) U.S. Cl. .................................. 73/25.03; 73/25.01
(58) Field of Classification Search ............. 73/25.03, 73/25.01, 25.05
   See application file for complete search history.

(56) References Cited

U.S. PATENT DOCUMENTS

| | | | |
|---|---|---|---|
| 4,141,955 A | | 2/1979 | Obiaya |
| 4,298,574 A | | 11/1981 | Bohl |
| 4,498,330 A | * | 2/1985 | Hosoya ................... 73/23.21 |
| 4,893,108 A | * | 1/1990 | Kolesar, Jr. ............... 338/34 |
| 5,362,975 A | * | 11/1994 | von Windheim et al. ..... 257/76 |
| 5,428,988 A | * | 7/1995 | Starkovich .................. 73/40 |
| 5,507,879 A | * | 4/1996 | Gyoten et al. ............. 136/224 |
| 5,670,115 A | * | 9/1997 | Cheng et al. ............... 422/90 |
| 5,756,878 A | * | 5/1998 | Muto et al. ................ 73/25.03 |
| 5,886,614 A | * | 3/1999 | Cheng et al. ............... 338/34 |
| 6,265,222 B1 | * | 7/2001 | DiMeo et al. ............. 436/144 |
| 6,436,346 B1 | * | 8/2002 | Doktycz et al. ............. 422/51 |
| 6,464,838 B1 | | 10/2002 | Charrin et al. |

(Continued)

FOREIGN PATENT DOCUMENTS

EP   0573961 A2   12/1993

(Continued)

OTHER PUBLICATIONS

McAleer et al., "Tin Dioxide Gas Sensors: Use of the Seebeck Effect," Nov. 1985, Sensors and Actuators, vol. 8, No. 3, pp. 251-257.

(Continued)

*Primary Examiner*—Michael Cygan
(74) *Attorney, Agent, or Firm*—Beyer Weaver & Thomas, LLP

(57) ABSTRACT

A hydrogen sensor includes a hydrogen-absorbing material, a thermoelectric element, an electrical circuit for driving the thermoelectric element, a thermometer for the hydrogen-absorbing material, a temperature control circuit for maintaining the hydrogen-absorbing material at a constant temperature using the thermoelectric element, a unit for calculating the exothermic value of the hydrogen-absorbing material based on the electrical current flowing from the drive circuit, and a unit for calculating the hydrogen uptake of the hydrogen-absorbing material based on the exothermic value.

6 Claims, 4 Drawing Sheets

U.S. PATENT DOCUMENTS

| | | | |
|---|---|---|---|
| 6,464,938 B1 * | 10/2002 | Rongier et al. | 422/51 |
| 6,838,287 B2 * | 1/2005 | Bonne et al. | 436/149 |
| 2005/0067281 A1 * | 3/2005 | Shimada et al. | 204/424 |
| 2005/0189223 A1 * | 9/2005 | Yamaguchi et al. | 204/431 |

FOREIGN PATENT DOCUMENTS

| | | | |
|---|---|---|---|
| EP | 1293769 A2 | | 3/2003 |
| JP | 02259458 A | * | 10/1990 |
| JP | 03272444 A | * | 12/1991 |
| JP | 2003-156461 | | 5/2003 |
| JP | 2003-156461 A | * | 5/2003 |

OTHER PUBLICATIONS

European Search Report dated Mar. 31, 2005 from corresponding European Application No. 04030635.9.

* cited by examiner

HYDROGEN SENSOR, APPARATUS FOR MEASURING HYDROGEN CONCENTRATION, AND METHOD FOR MEASURING HYDROGEN CONCENTRATION

BACKGROUND OF THE INVENTION

1. Field of the Invention

The present invention relates to a hydrogen sensor, and particularly to a hydrogen sensor for detecting a very small amount of hydrogen. The present invention also relates to a method for measuring hydrogen concentration using the sensor.

2. Description of the Related Art

Sensors that include hydrogen-absorbing materials are already known. Physical properties, such as electrical resistance, weight, and strain (internal stress), of the hydrogen-absorbing materials vary during the hydrogen absorption and thereby the sensors can detect the amount of hydrogen.

Japanese Unexamined Patent Application Publication No. 2003-156461 discloses a sensor having a thermoelectric element for detecting an exothermic value. The thermoelectric element detects a temperature increase caused by hydrogen absorption as a thermoelectromotive force.

However, temperature variations of a hydrogen-absorbing material may change the hydrogen absorbing characteristics, in particular, an initial hydrogen partial pressure of the hydrogen absorption; therefore, the hydrogen concentration derived from the variations in the physical properties of the hydrogen-absorbing material may undesirably vary over time.

In conventional techniques, the variations in the hydrogen absorbing characteristics must occasionally be compensated for as a result of the temperature variation. This makes the precise measurement of the hydrogen concentration difficult.

This problem can be overcome by keeping the temperature of the hydrogen-absorbing material constant. When the electrical resistance of the hydrogen-absorbing material is utilized, for example, the measurement requires "an electrical resistance detector," "a cooler," "a temperature controller," and "a unit for calculating hydrogen concentration." That is, a cooling system and a temperature controller must be introduced, making an apparatus and a circuit more complex.

SUMMARY OF THE INVENTION

Accordingly, it is an object of the present invention to provide a method for measuring hydrogen concentration more precisely by keeping the temperature of a hydrogen-absorbing material constant.

Another object of the present invention is to provide a simple hydrogen sensor that includes a thermoelectric element. Both cooling of a hydrogen-absorbing material (to keep the temperature constant) during hydrogen absorption and the detection of hydrogen can be achieved by the thermoelectric element alone.

A hydrogen sensor according to the present invention comprises:

a hydrogen-absorbing material;

a thermoelectric element that transfers heat with the hydrogen-absorbing material;

an electrical circuit for driving the thermoelectric element;

a thermometer for the hydrogen-absorbing material;

a temperature control circuit for maintaining the hydrogen-absorbing material at a constant temperature by controlling electrical current flowing to the thermoelectric element;

a unit for calculating the exothermic value of the hydrogen-absorbing material (the energy for cooling the thermoelectric element) from variations in the electrical current flowing from the drive circuit; and a unit for calculating the hydrogen uptake of the hydrogen-absorbing material from the exothermic value.

Preferably, the hydrogen-absorbing material according to the present invention is a thin film or a resin composite formed on a surface of the thermoelectric element.

The hydrogen-absorbing material according to the present invention may rapidly increase the hydrogen uptake when the hydrogen concentration exceeds a specific threshold at a predetermined temperature.

An apparatus for measuring the hydrogen concentration according to the present invention includes the hydrogen sensor described above and a gas temperature controller for adjusting the temperature of a gas to be measured to a predetermined temperature.

A method for measuring a hydrogen concentration according to the present invention comprises measuring the hydrogen concentration with the hydrogen sensor while the hydrogen-absorbing material is maintained at a predetermined temperature.

Another method for measuring a hydrogen concentration according to the present invention comprises measuring the hydrogen concentration with the apparatus for measuring the hydrogen concentration while the temperatures of the test gas and the hydrogen-absorbing material are kept constant.

In the hydrogen sensor according to the present invention, cooling of the hydrogen-absorbing material and the measurement of the hydrogen concentration are simultaneously performed with the thermoelectric element. Thus, the hydrogen sensor, the apparatus including the hydrogen sensor, and their circuitry have simple structures. This reduces their manufacturing cost. In addition, the constant temperature of the hydrogen-absorbing material eliminates time-dependent variations in physical properties and thus allows for precise measurement of the hydrogen concentration.

Since the hydrogen-absorbing material according to the present invention is a thin film or a resin composite formed on a surface of the thermoelectric element, the temperature difference between the hydrogen-absorbing material and the thermoelectric element is small. Thus, the hydrogen-absorbing material can be more precisely maintained at a constant temperature. In addition, the endothermic value of the thermoelectric element, which is equal to the exothermic value of the hydrogen-absorbing material and is determined by the temperature difference between the hydrogen-absorbing material and the thermoelectric element, can be more precisely calculated. Finally, the hydrogen concentration can also be more precisely calculated from the endothermic value or the exothermic value.

The gas temperature controller prevents the sensor from misidentifying temperature variations of the test gas as the presence of hydrogen.

In the method for measuring a hydrogen concentration according to the present invention, the hydrogen concentration is measured with the hydrogen sensor including the thermoelectric element while the hydrogen-absorbing material is simultaneously maintained at a predetermined temperature. Thus, the hydrogen concentration can be measured precisely without being affected by time-dependent variations in the physical properties.

Furthermore, in the method for measuring the hydrogen concentration according to the present invention, the hydrogen concentration is measured with the hydrogen sensor while the test gas and the hydrogen-absorbing material are maintained at predetermined temperatures. Thus, the hydrogen concentration can precisely be calculated from the endothermic value.

DESCRIPTION OF THE PREFERRED EMBODIMENTS

Figure 1:
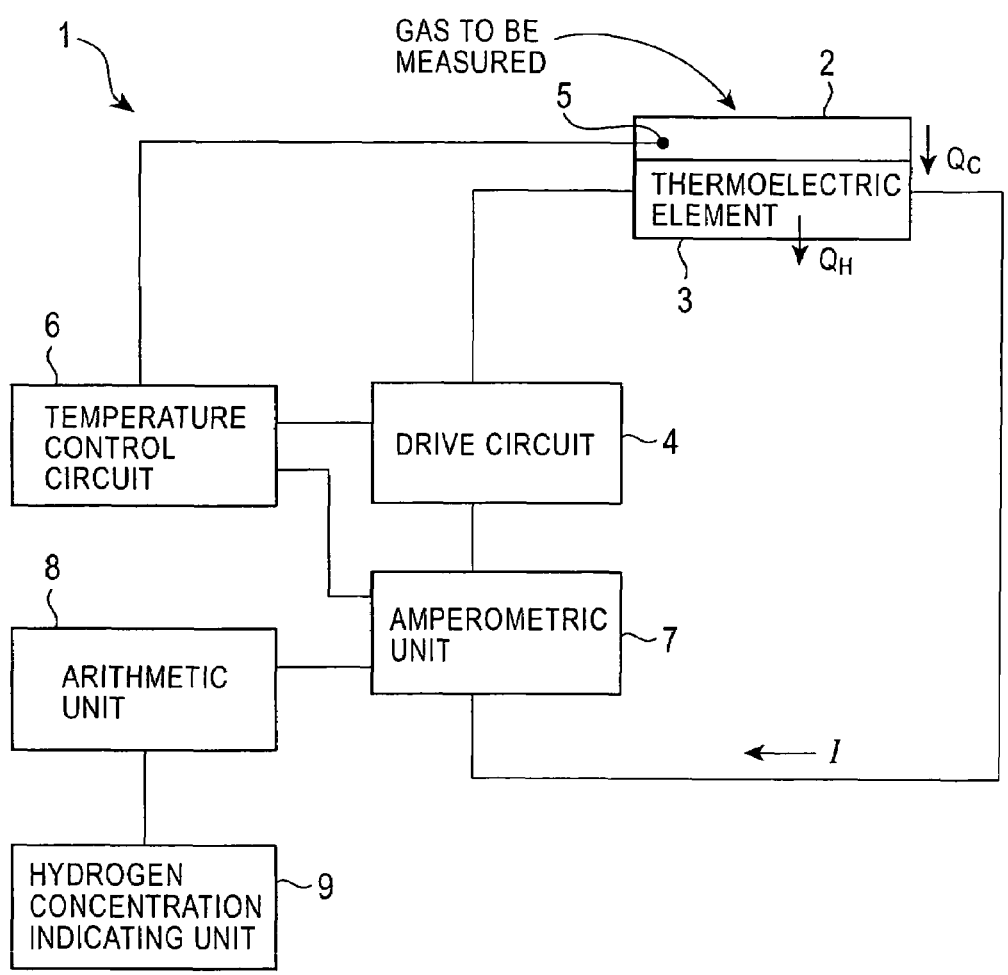
FIG. 1 is a block diagram of a hydrogen sensor according to a first embodiment of the present invention.

A hydrogen sensor according to a first embodiment of the present invention will now be described with reference to the drawings. FIG. 1 is a block diagram of a hydrogen sensor 1 according to the first embodiment of the present invention.

The hydrogen sensor 1 includes a hydrogen-absorbing material 2; a thermoelectric element 3, which transfers heat to and from the hydrogen-absorbing material 2; a drive circuit 4 connected to the thermoelectric element 3; a temperature sensor 5 for the hydrogen-absorbing material 2; a temperature control circuit 6 for maintaining the temperature of the hydrogen-absorbing material 2 with the thermoelectric element 3 in response to the output of the temperature sensor 5; an amperometric unit 7 for calculating the exothermic value (endothermic value) of the hydrogen-absorbing material 2 based on the current from the drive circuit 4; an arithmetic unit 8 for calculating the hydrogen uptake of the hydrogen-absorbing material 2 based on the exothermic value; and a hydrogen concentration indicating unit 9 for indicating the output of the arithmetic unit 8.

Figure 2:
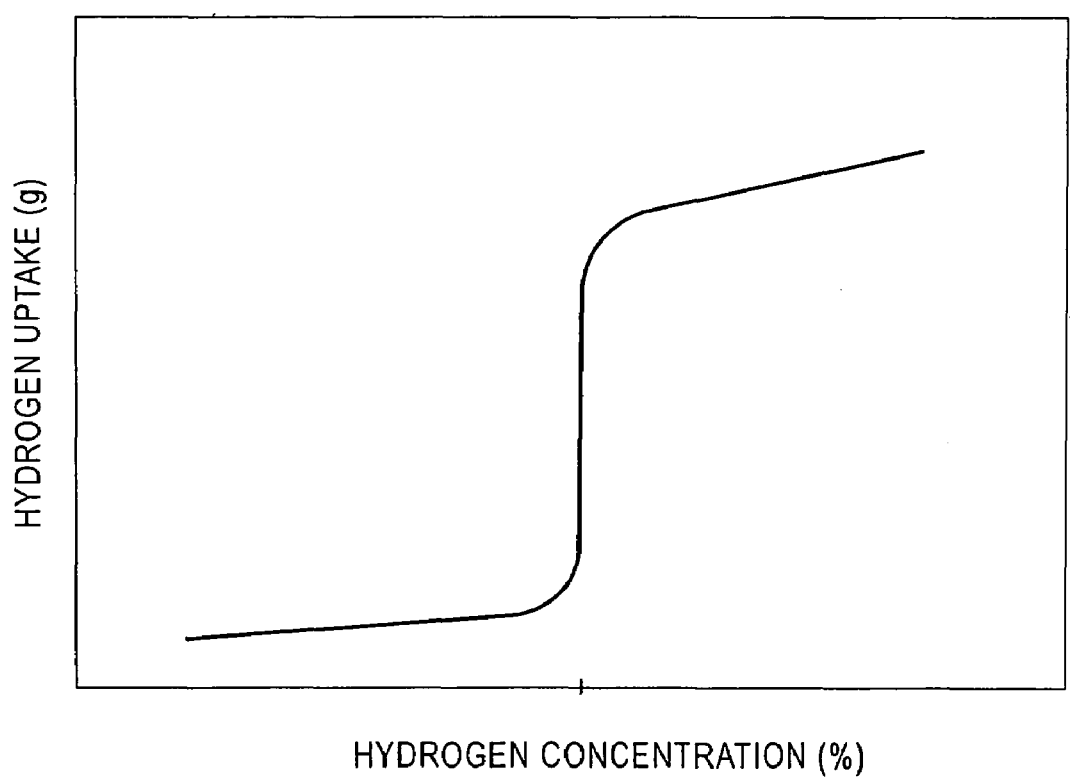
FIG. 2 is a schematic graph showing a relationship between hydrogen concentration and hydrogen uptake of a hydrogen-absorbing material according to the present invention.

The hydrogen-absorbing material 2 is a composite (mixture) of an alloy powder and a binder resin described below, and is formed on a surface of the thermoelectric element 3. The hydrogen-absorbing material 2 generates heat when it absorbs hydrogen, and rapidly increases the hydrogen uptake when the hydrogen concentration exceeds a specific threshold, as shown in FIG. 2.

Examples of the alloy include a Pd-based alloy, a ZrNi alloy, a ZrCr alloy, a TiMn alloy, a TiFeMn alloy, a TiFeZrNb alloy, a FeTiO alloy, a MgNi alloy, a CaNi alloy, a LaNi alloy, and a LaNiAl alloy. Preferably, the alloy is in a powder form having a particle size of about 30 μm or less.

The binder resin may be composed of benzocyclobutene and a solvent, such as mesitylene.

The temperature sensor 5 may be a thermocouple embedded in or attached to the hydrogen-absorbing material 2. The temperature sensor 5 is connected to the temperature control circuit 6 and generates a voltage signal in response to temperature variations of the hydrogen-absorbing material 2.

The drive circuit 4 outputs a driving voltage to the thermoelectric element 3. At a steady state (that is, before detecting hydrogen), the driving voltage is maintained at a sufficient voltage to maintain the hydrogen-absorbing material 2 at a preset temperature. This preset temperature depends on the composition of the hydrogen-absorbing material 2 and the hydrogen concentration range to be measured.

Figure 3:
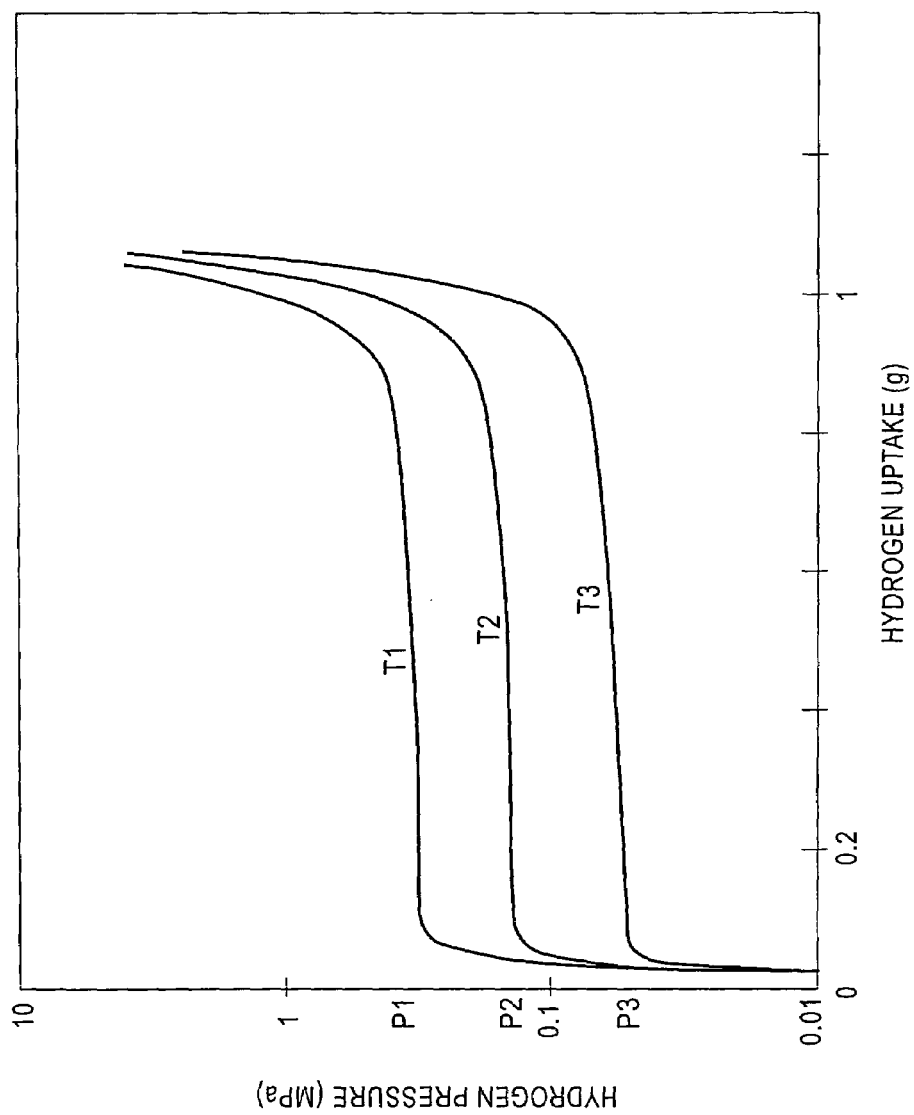
FIG. 3 is a schematic graph showing a relationship between hydrogen uptake and hydrogen pressure of a hydrogen-absorbing material according to the present invention.

As shown in FIG. 3, the hydrogen-absorbing material 2 has different hydrogen pressure thresholds P (corresponding to concentrations), at which the hydrogen uptake increases rapidly, depending on the temperature; it has a hydrogen pressure threshold P1 at a temperature of T1, P2 at a temperature of T2, and P3 at a temperature of T3 (T3<T2<T1; for example, T3=20° C., T2=40° C., and T1=60° C.).

The hydrogen-absorbing material 2 generates heat when it absorbs hydrogen. For example, a LaNi alloy generates heat of about 30 kJ per mole of absorbed hydrogen, and a LaNiAl alloy generates 30–40 kJ per mole of absorbed hydrogen, depending on the composition.

The output power of the drive circuit 4 is controlled by the temperature control circuit 6 so that the temperature of the hydrogen-absorbing material 2 detected by the temperature sensor 5 remains constant.

The thermoelectric element 3 utilizes a Peltier element, which generates heat on one surface and absorbs heat on the other surface due to the passage of the current. The exothermic surface and the endothermic surface of the Peltier element are reversed with a reverse in the current direction.

The amperometric unit 7 measures the driving current I supplied to the thermoelectric element 3 by the drive circuit 4. The arithmetic unit 8 calculates the endothermic value Q of the thermoelectric element 3, that is, the amount of heat Q absorbed by the thermoelectric element 3 from the hydrogen-absorbing material 2. As a result, the exothermic value (endothermic value) and the hydrogen uptake of the hydrogen-absorbing material 2 are calculated.

In the hydrogen sensor shown in FIG. 1, the temperature of a test gas is assumed to be constant. Thus, for a test gas having a varying temperature, a gas temperature controller is required to maintain the gas at a predetermined temperature.

The mechanism of measuring the hydrogen concentration with the hydrogen sensor 1 will be described below. In this description, the ambient temperature of the hydrogen sensor 1, that is, the temperature of the test gas is assumed to be constant. The preset temperature of the hydrogen-absorbing material 2 is assumed to be lower than the ambient temperature.

At a steady state where the test gas contains no hydrogen, the drive circuit 4 supplies sufficient power to the thermoelectric element 3 to maintain the hydrogen-absorbing material 2 at a preset temperature. The endothermic value Q to maintain the preset temperature is equal to the amount of heat supplied to the hydrogen-absorbing material 2 by the test gas. At the same time, the temperature sensor 5 sends a voltage signal corresponding to the preset temperature to the temperature control circuit 6.

The temperature control circuit 6 stores the preset temperature of the thermoelectric element 3, that is, the preset temperature of the hydrogen-absorbing material 2, and sends a required voltage signal to the drive circuit 4. The temperature control circuit 6 also stores the voltage signal from the temperature sensor 5 at the steady state.

For the test gas containing hydrogen, the hydrogen-absorbing material 2 absorbs hydrogen and generates heat $Q_c$ per unit time. When the temperature sensor 5 detects a deviation of the temperature of the hydrogen-absorbing material 2 from the steady state, the temperature control circuit 6 instructs the drive circuit 4 to adjust the current I so as to maintain the hydrogen-absorbing material 2 at the constant temperature. Then, the generated heat $Q_c$ of the hydrogen-absorbing material 2 is absorbed by the thermoelectric element 3. This heat $Q_c$ and the heat generated by the passage of the current I are dissipated from the opposite surface at an amount of $Q_H$ per unit time.

The amperometric unit 7 measures the current I, which is supplied to the thermoelectric element 3 and varies with the driving voltage, and sends a signal based on the current I to the arithmetic unit 8.

The arithmetic unit 8 calculates the total endothermic value Qc of the thermoelectric element 3, that is, the total exothermic value of the hydrogen-absorbing material 2 by integrating the variations of the current I relative to the steady state.

The endothermic value Q [W] per unit time is determined by the following equation (1):

$$Q = \alpha e \ Tc \ I - ReI^2/2 - Ke\Delta T \quad (1)$$

wherein,
αe: Seebeck coefficient [V/K]
Tc: temperature on the cooling surface [K], that is, temperature of the temperature sensor 5
I: current [A]
Re: electrical resistance of the thermoelectric element 3 [Ω]
Ke: thermoelectric power of the thermoelectric element 3 [W/cm K]
ΔT: temperature difference between the dissipation surface and the cooling surface, that is, between the temperature sensor 5 and the ambient temperature Integration of the equation (1) over the time period when the temperature deviates from the steady state yields the total endothermic value Qc [Wh].

The total endothermic value Qc is equal to the total exothermic value of the hydrogen-absorbing material 2. The total exothermic value is a function of the hydrogen uptake of the hydrogen-absorbing material 2. Since the hydrogen-absorbing material 2 absorbs little hydrogen below a predetermined hydrogen pressure threshold and absorbs a large amount of hydrogen over the threshold, as shown in FIG. 3, the driving current I suddenly increases when the hydrogen concentration of the test gas exceeds the predetermined threshold.

The arithmetic unit 8 calculates the endothermic value Q of the thermoelectric element 3, that is, the exothermic value of the hydrogen-absorbing material 2 from the increase in the driving current I. The arithmetic unit 8 also calculates the hydrogen concentration of the test gas based on the hydrogen uptake of the hydrogen-absorbing material 2. Then, the arithmetic unit 8 sends the results to the hydrogen concentration indicating unit 9, which displays the resulting hydrogen concentration.

In this way, hydrogen in the test gas exceeding the predetermined hydrogen pressure threshold can be detected.

In the hydrogen sensor 1 according to the present embodiment, cooling of the hydrogen-absorbing material 2 and the measurement of the hydrogen concentration are simultaneously performed with the thermoelectric element 3. Thus, the hydrogen sensor 1, the apparatus including the hydrogen sensor 1, and their circuitry have simple structures. This reduces their manufacturing cost. In addition, the constant temperature of the hydrogen-absorbing material 2 eliminates the temperature-dependent variations in the physical properties and thus allows for precise measurement of the hydrogen concentration of the test gas.

Furthermore, since the hydrogen-absorbing material 2 is a thin film or a resin composite formed on a surface of the thermoelectric element 3, the temperature difference between the hydrogen-absorbing material 2 and the thermoelectric element 3 is small. Thus, the hydrogen-absorbing material 2 can be precisely maintained at a constant temperature. Hence, the endothermic value Q of the thermoelectric element 3, which is equal to the exothermic value of the hydrogen-absorbing material 2, can precisely be converted into the hydrogen concentration.

The gas temperature controller 6 prevents the sensor from misidentifying temperature variations of the test gas around the hydrogen sensor 1 as the presence of hydrogen.

In the hydrogen sensor of the present embodiment, the test gas has the same temperature as the ambient temperature, which is kept substantially constant. Thus, the thermoelectric element 3 does not need to compensate for temperature variations of the test gas. This prevents the misoperation of the hydrogen sensor caused by the temperature variations.

A hydrogen sensor and an apparatus for measuring hydrogen according to a second embodiment of the present invention will now be described with reference to the drawings.

Figure 4:
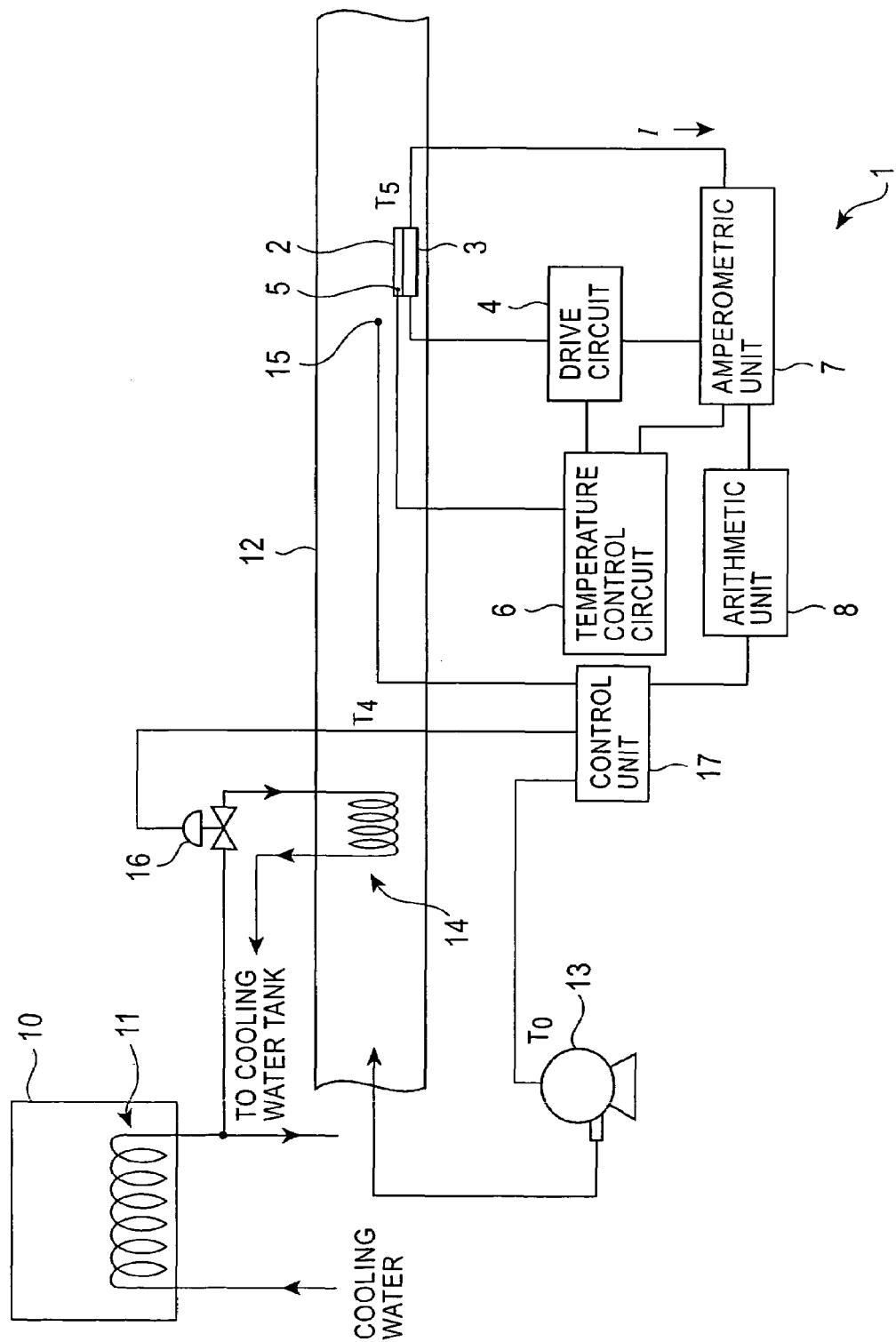
FIG. 4 is a block diagram of a hydrogen sensor and an apparatus for measuring a hydrogen concentration according to a second embodiment of the present invention.

FIG. 4 is a block diagram showing a hydrogen measuring apparatus according to the present embodiment. Like components are denoted by like numerals in the first embodiment and will not be further explained.

A hydrogen sensor 1 according to the present embodiment is designed for a fuel cell vehicle to detect a hydrogen leak.

The hydrogen measuring apparatus includes a fuel cell 10 provided with a heat exchanger 11 through which cooling water passes, a tube 12 for measuring the hydrogen concentration in a test gas, a pump 13 for feeding the test gas into the measuring tube 12, a heat exchanger 14 to which the cooling water flows from the heat exchanger 11, a thermometer 15 for measuring the temperature around the hydrogen sensor 1 within the measuring tube 12, and a flow valve 16 for controlling the cooling water to the heat exchanger 14. The flow valve 16 is controlled by a control unit 17 in response to a signal from the thermometer 15.

A test gas having an ambient temperature T0 is sampled by the pump 13, is heated to T4 with the heat exchanger 14, and is fed to the hydrogen-absorbing material 2, the temperature sensor 5, and the thermoelectric element 3. The hydrogen-absorbing material 2 is maintained at a temperature T5 specific to the material. Preferably, these temperatures are set to be T4≧T5>T0. The temperature T5 remains constant by slight cooling with the thermoelectric element 3. The temperature increase from T0 to T4 is achieved by supplying a part of the heated cooling water from the fuel cell 10 to the heat exchanger 14. The flow rate of the heated cooling water is regulated by the flow valve 16 controlled by the control unit 17.

The present embodiment has the same effect as in the first embodiment. In addition, while the temperature T5 remains constant by the slight cooling with the thermoelectric element 3, the presence of hydrogen increases the endothermic value (increases the current in the same direction as in the steady state) and does not reverse the direction of the current. Thus, it is very easy to control the temperature of the thermoelectric element 3.

What is claimed is:
1. A hydrogen sensor comprising:
a hydrogen-absorbing material;

a thermoelectric element that transfers heat to and from the hydrogen-absorbing material;

an electrical circuit configured to drive the thermoelectric element and to cool the hydrogen-absorbing material;

a thermometer configured to determine a temperature of the hydrogen-absorbing material;

a temperature control circuit for maintaining the hydrogen-absorbing material at a constant temperature which has a same temperature as an ambient temperature without heat transfer with a gas to be sensed by controlling electrical current flowing to the thermoelectric element;

a unit for calculating the exothermic value of the hydrogen-absorbing material based on variations in the electrical current flowing from the drive circuit by determining a cooling heat value which the thermoelectric element requires to cool the hydrogen-absorbing material, the exothermic value having a same value as the cooling heat value; and a unit for calculating the hydrogen uptake of the hydrogen-absorbing material based on the exothermic value.

2. The hydrogen sensor according to claim 1, wherein the hydrogen-absorbing material is a thin film or a resin composite formed on a surface of the thermoelectric element.

3. The hydrogen sensor according to claim 2, wherein the hydrogen-absorbing material rapidly increases the hydrogen uptake when the hydrogen concentration exceeds a specific threshold at a predetermined temperature.

4. An apparatus for measuring the hydrogen concentration comprising:

a hydrogen sensor according to claim 1; and a gas temperature controller for adjusting the temperature of a gas to be measured for hydrogen concentration to a predetermined temperature.

5. A method for measuring the hydrogen concentration with a hydrogen sensor according to claim 1 while the temperature of a hydrogen-absorbing material is kept constant.

6. A method for measuring the hydrogen concentration with an apparatus for measuring the hydrogen concentration according to claim 4 while the temperatures of a gas to be measured and a hydrogen-absorbing material are kept constant.

* * * * *